United States Patent [19]

Bonse et al.

[11] Patent Number: 4,960,783
[45] Date of Patent: Oct. 2, 1990

[54] USE OF BENZIMIDAZOLE DERIVATIVES AS YIELD PROMOTERS

[75] Inventors: Gerhard Bonse, Cologne; Werner Hallenbach, Langenfeld; Hans Lindel, Leverkusen; Friedrich Berschauer, Wuppertal, all of Fed. Rep. of Germany

[73] Assignee: Bayer Aktiengesellschaft, Leverkusen, Fed. Rep. of Germany

[21] Appl. No.: 292,581

[22] Filed: Dec. 30, 1988

[30] Foreign Application Priority Data

Jan. 5, 1988 [DE] Fed. Rep. of Germany ....... 3800096

[51] Int. Cl.$^5$ ........................................... C07D 235/08
[52] U.S. Cl. .................... 514/387; 514/394; 548/325; 548/330; 548/332; 548/305
[58] Field of Search ................ 514/387, 394; 548/325, 548/330, 332, 305

[56] References Cited

U.S. PATENT DOCUMENTS

| | | | |
|---|---|---|---|
| 3,982,012 | 9/1976 | Fauland et al. | 548/325 X |
| 4,070,478 | 1/1978 | Talaty et al. | 548/325 X |
| 4,140,789 | 2/1979 | Jaeggi et al. | 548/308 X |
| 4,204,069 | 5/1980 | Arnett et al. | 548/325 |
| 4,721,717 | 1/1988 | Friebe et al. | 514/394 X |

FOREIGN PATENT DOCUMENTS 3697 11/1965 France .
1559915 1/1980 United Kingdom .

OTHER PUBLICATIONS

Chodnekar et al., "B–Adrenergic Blocking Agents . . . ", Journal of Medicinal Chemistry, vol. 15, No. 1, Jan. 1972, pp. 49–57.
Arneh, et al., "Synthesis and Adrenergic . . . ", Journal of Medicinal Chemistry, vol. 21, No. 1, Jan. 1978, pp. 72–78.

*Primary Examiner*—Mary C. Lee
*Assistant Examiner*—Catherine Scalzo

*Attorney, Agent, or Firm*—Sprung Horn Kramer & Woods

[57] ABSTRACT

Method of promoting the yield and growth of animals which comprises administering to such animals a yield and growth promoting effective amount of a benzimidazole derivative of the formula

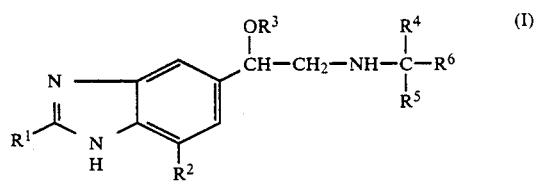

in which
R$^1$ stands for hydrogen, hydroxyl, alkyl or halogenoalkyl,
R$^2$ stands for hydrogen, alkyl, halogen, CN or halogenalkyl,
R$^3$ stands for hydrogen, alkyl or acyl,
R$^4$ stands for hydrogen, alkyl or halogenoalkyl,
R$^5$ stands for alkyl or halogenoalkyl,
R$^6$ stands for alkyl or cycloalkyl, which is optionally substituted by halogen, cycloalkyl, OH, alkoxy, halogenoalkoxy or aryl, which can in turn be substituted by alkyl, halogen, CN or the radicals —COR$^7$, —O—alkylene—COR$^7$, —alkylene—R$^8$ or —O— alkylene—R$^8$,
R$^7$ stands for hydroxyl, alkoxy or —NR$^9$R$^{10}$,
R$^8$ stands for hydroxyl, alkoxy or —NR$^9$R$^{10}$,
R$^9$ stands for hydrogen or alkyl and
R$^{10}$ stands for hydrogen or alkyl, or physiologically tolerated salts thereof. The active materials are new except for those in which
R$^1$ stands for hydrogen,
R$^4$ stands for hydrogen,
R$^5$ stands for methyl and
R$^6$ stands for methyl.

8 Claims, No Drawings

USE OF BENZIMIDAZOLE DERIVATIVES AS YIELD PROMOTERS

The present invention relates to the use of benzimidazole derivatives as yield promoters for animals, new benzimidazole derivatives and intermediates and processes for their preparation.

1-(5-Benzimidazolyl)-2-aminoethanol and -2-isopropylaminoethanol are known (British Patent No. 1,559,915). However, nothing is known of their suitability as yield promoters for animals.

The present invention relates to:

1. The use of benzimidazole derivatives of the formula I

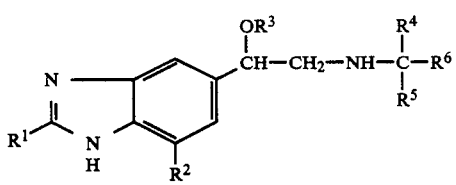

in which
  $R^1$ stands for hydrogen, hydroxyl, alkyl or halogenoalkyl,
  $R^2$ stands for hydrogen, alkyl, halogen, CN or halogenoalkyl,
  $R^3$ stands for hydrogen, alkyl or acyl,
  $R^4$ stands for hydrogen, alkyl or halogenoalkyl,
  $R^5$ stands for alkyl or halogenoalkyl,
  $R^6$ stands for alkyl or cycloalkyl, which is optionally substituted by halogen, cycloalkyl, OH, alkoxy, halogenoalkoxy or aryl, which can in turn be substituted by alkyl, halogen, CN or the radicals —COR$^7$, —O—alkylene-COR$_7$, —alkylene-R$^8$ or —O—alkylene-$^8$,
  $R^7$ stands for hydroxyl, alkoxy or —NR$^9$R$^{10}$,
  $R^8$ stands for hydroxyl, alkoxy or —NR$^9$R$^{10}$,
  $R^9$ stands for hydrogen or alkyl and
  $R^{10}$ stands for hydrogen or alkyl, and tautomers and physiological; tolerated salts thereof for promoting the yield and growth of animals.

2. New benzimidazole derivatives of the formula I

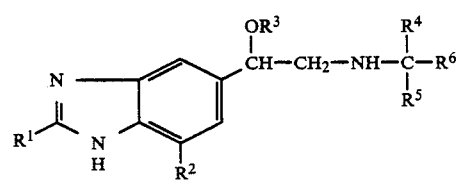

in which
  $R^1$ stands for hydrogen, hydroxyl, alkyl or halogenoalkyl,
  $R^2$ stands for hydrogen, alkyl, halogen, CN or halogenoalkyl,
  $R^3$ stands for hydrogen, alkyl or acyl,
  $R^4$ stands for hydrogen, alkyl or halogenoalkyl,
  $R^5$ stands for alkyl or halogenoalkyl,
  $R^6$ stands for alkyl or cycloalkyl, which is optionally substituted by halogen, cycloalkyl, OH, alkoxy, halogenoalkoxy or aryl, which can in turn be substituted by alkyl, halogen, CN or the radicals —COR$^7$, —O-alkylene—COR$^7$, alkylene-R$^8$ or —O—alkylene-R$^8$,
  $R^7$ stands for hydroxyl, alkoxy or —NR$^9$R$^{10}$,
  $R^8$ stands for hydroxyl, alkoxy or —NR$^9$R$^{10}$,
  $R^9$ stands for hydrogen or alkyl and
  $R^{10}$ stands for hydrogen or alkyl,
and tautomers and physiologically tolerated salts thereof, excluding compounds in which
  $R^1$ stands for hydrogen,
  $R^4$ stands for hydrogen,
  $R^5$ stands for methyl and
  $R^6$ stands for methyl,
and tautomers and salts thereof.

3. Process for the preparation of the new benzimidazole derivatives of formula I

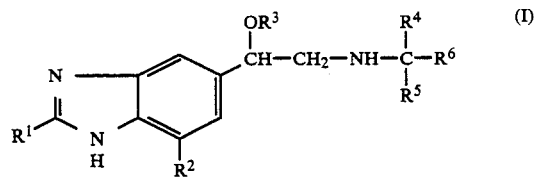

in which
  $R^1$ stands for hydrogen, hydroxyl, alkyl or halogenoalkyl,
  $R^2$ stands for hydrogen, alkyl, halogen, CN or halogenoalkyl,
  $R^3$ stands for hydrogen, alkyl or acyl,
  $R^4$ stands for hydrogen, alkyl or halogenoalkyl,
  $R^5$ stands for alkyl or halogenoalkyl,
  $R^6$ stands for alkyl or cycloalkyl, which is optionally substituted by halogen, cycloalkyl, OH, alkoxy, halogenoalkoxy or aryl, which can in turn be substituted by alkyl, halogen, CN or the radicals —COR$^7$, —O-alkylene-COR$^7$, -alkylene-R$^8$ or —O—alkylenel-R$^8$,
  $R^7$ stands for hydroxyl, alkoxy or —NR$^9$R$^{10}$,
  $R^8$ stands for hydroxyl, alkoxy or —NR$^9$R$^{10}$,
  $R^9$ stands for hydrogen or alkyl and
  $R^{10}$ stands for hydrogen or alkyl,
and tautomers and physiologically tolerated salts thereof, excluding compounds in which $R^1$ and $R^4$ stand for hydrogen and $R^5$ and $R^6$ stand for methyl, characterized in that (a) halogenomethyl ketones of the formula II

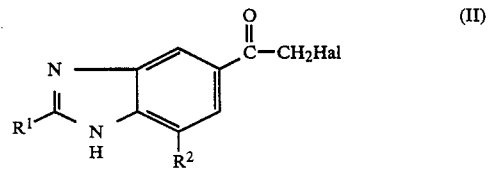

in which
  $R^1$ and $R^2$ have the abovementioned meaning and
  Hal represents halogen, are reacted with amines of the formula III

in which

R⁴ to R⁶ have the abovementioned meaning, and the carbonyl group is subsequently reduced, or (b) β-halogenoethyl compounds of the formula IV

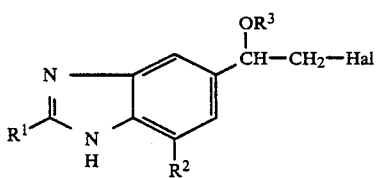

in which
R¹ to R³ have the abovementioned meaning and Hal represents halogen, are reacted with amines of the formula III

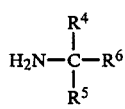

in which
R⁴ to R⁶ have the abovementioned meaning, or (c) in the case where R⁴ in formula I stands for hydrogen, in that compounds of the formula V

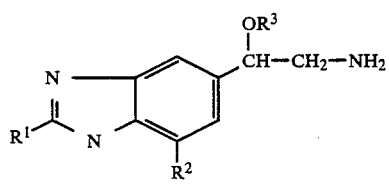

in which
R¹ to R³ have the abovementioned meaning, are reacted with compounds of the formula VI

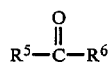

in which
R⁵ and R⁶ have the abovementioned meaning, under reducing conditions, or (d) compounds of the formula VII

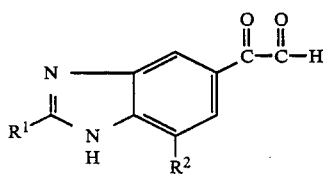

in which
R¹ and R² have the abovementioned meaning, are reacted with amines of the formula III

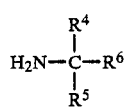

in which

R⁴ to R⁶ have the abovementioned meaning, under reducing conditions.

4. New compounds of the formula II

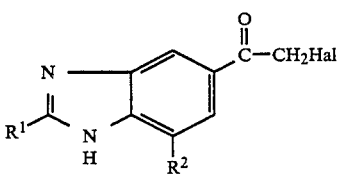

in which
R¹ stands for hydrogen,
R² stands for hydrogen, alkyl or halogen and Hal stands for halogen.

5. Process for the preparation of the new compounds of the formula II according to (4), characterized in that acetyl compounds of the formula VIII

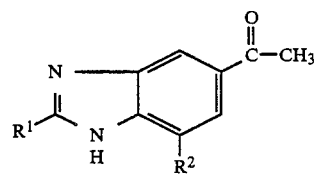

in which
R¹ stands for hydrogen and
R² stands for hydrogen, alkyl or halogen,
(a) are reacted with elemental halogen, or
(b) are reacted with copper halides of the formula Cu-Hal₂.

6. New compounds of the formula VIII

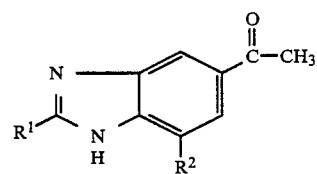

in which
R¹ stands for hydrogen and
R² stands for hydrogen, alkyl or halogen.

7. Process for the preparation of the compounds of the formula VIII according to (6), characterized in that 3,4-diaminoacetophenones of the formula IX

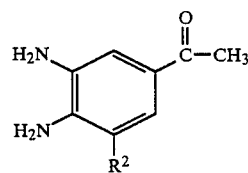

in which
R² stands for hydrogen, alkyl or halogen, are reacted with formic acid in the presence of inorganic acids.

8. New compounds of the formula IV (IV)

[Structure IV: benzimidazoline with CH(OH)-CH2-Hal substituent, R1 on C=N, R2 on ring]

in which
R[1] stands for hydrogen, hydroxyl, alkyl or halogenoalkyl and
R[2] stands for hydrogen, alkyl, halogen, CN or halogenoalkyl.

9. Process for the preparation of the compounds of the formula IV according to (8), characterized in that compounds of the formula II (II)

[Structure II: benzimidazoline with C(O)-CH2Hal substituent]

in which
R[1] and R[2] have the meanings given in the case of (8), are reduced.

10. New compounds of the formula V (V)

[Structure V: benzimidazoline with CH(OH)-CH2-NH2 substituent]

in which
R[1] stands for hydrogen, alkyl or halogenoalkyl and
R[2] stands for alkyl, halogen, CN or halogenoalkyl.

11. Process for the preparation of the compounds of the formula V according to (10), characterized in that compounds of the formula X (X)

[Structure X: O2N and O=C-N(R1)H substituents on benzene ring with CH(OH)-CH2-NO2]

in which
R[1] and R[2] have the meaning given in the case of 10 (above),
are reduced with hydrogen in the presence of catalysts.

12. New compounds of the formula VII (VII)

[Structure VII: benzimidazoline with C(O)-C(O)H (glyoxal) substituent]

in which
R[1] stands for hydrogen, hydroxyl, alkyl or halogenoalkyl and
R[2] stands for hydrogen, alkyl, halogen, CN or halogenoalkyl.

13. Process for the preparation of the compounds of the formula VII according to (12), characterized in that
(a) compounds of the formula II (II)

[Structure II: benzimidazoline with C(O)-CH2Hal substituent]

in which
R[1] and R[2] have the meaning given above in the case of (12) and
Hal stands for halogen,
or
(b) compounds of the formula VIII (VIII)

[Structure VIII: benzimidazoline with C(O)-CH3 substituent]

in which
R[1] and R[2] have the meaning given in the case of (12)
are oxidized.

The compounds of the formula I are known in some cases. The known compounds have bronchodilatory action. They also reduce the intraocular pressure.

Compounds of the formula I can be used as yield promoters in animals and in particular for promoting the growth of animals.

The compounds of the formula I can also exist in the form of their racemates and as mixtures of the forms which are diastereomeric or enantiomeric to one another.

Physiologically tolerated salts of the compounds of the formula I can be formed with the following acids: hydrochloric acid, sulphuric acid, phosphoric acid, perchloric acid, hydrobromic and hydro acid, nitric acid, acetic acid, oxalic acid, malonic acid, succinic acid, ascorbic acid, malic acid, tartaric acid, maleic acid, fumaric acid, methanesulphonic acid, benzoic acid, substituted benzoic acids, formic acid, toluenesulphonic acid, benzenesulphonic acid, phthalic acid, naphthalenesulphonic acid, nicotinic acid, palmitic acid and embonic acid.

Preferred compounds of the formula I are those in which $R^1$ stands for H or OH,
$R^2$ stands for H, halogen, CN or halogenoalkyl,
$R^3$ stands for H,
$R^4$ stands for H or $C_{1-4}$-alkyl,
$R^5$ stands for $C_{1-4}$ alkyl,
$R^6$ stands for $C_{1-4}$-alkyl, which is optionally substituted by halogen, OH, $C_{1-4}$-alkoxy, $C_{1-4}$-halogenoalkoxy or phenyl, which is optionally substituted by $C_{1-4}$-alkyl, $COR^7$, —O—$C_{1-3}$-alkylene-$COR^7$, $C_{1-3}$-alkylene-$R^8$ or O—$C_{1-3}$-alkylene-$R^8$,
$R^7$ stands for OH, $C_{1-4}$-alkoxy, amino, methylamino or dimentylamino and
$R^8$ stands for OH, $C_{1-4}$-alkoxy, amino, methylamino or dimethylamino.

Particularly preferred compounds of the formula I are those in which
$R^1$ stands for hydrogen or OH,
$R^2$ stands for hydrogen, chlorine, bromine or trifluoromethyl,
$R^3$ stands for hydrogen,
$R^4$ stands for hydrogen or methyl,
$R^5$ stands for methyl and
$R^6$ stands for methyl, which is optionally substituted by OH or phenyl, which is in turn optionally substituted by methyl, ethyl, methoxyethyl, hydroxyethyl, methoxyethoxy or hydroxyethoxy.

The following compounds of the formula I may be mentioned specifically, in addition to the examples:

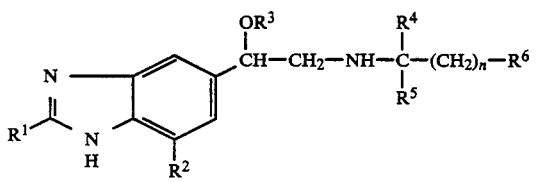

| $R^1$ | $R^2$ | $R^3$ | $R^4$ | $R^5$ | n | $R^6$ |
|---|---|---|---|---|---|---|
| H | H | H | H | $CH_3$ | 1 | H |
| H | H | H | $CH_3$ | $CH_3$ | 1 | OH |
| OH | H | H | H | $CH_3$ | 1 | H |
| OH | Cl | H | $CH_3$ | $CH_3$ | 1 | H |
| H | H | H | H | $CH_3$ | 1 | $C_6H_5$ |

The new compounds of the formula I can be prepared by the processes described 3 a–d.

If 4-cloro-6-benzimidazolylbromomethyl ketone is used as the compound of the formula II and tert.-butylamine is used as the amine of the formula III in process 3a), process 3a) can be represented by the following equation:

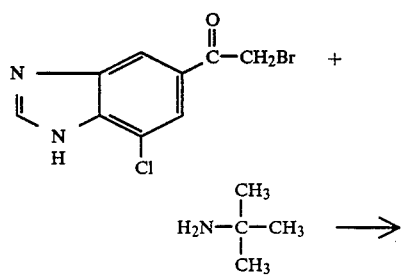

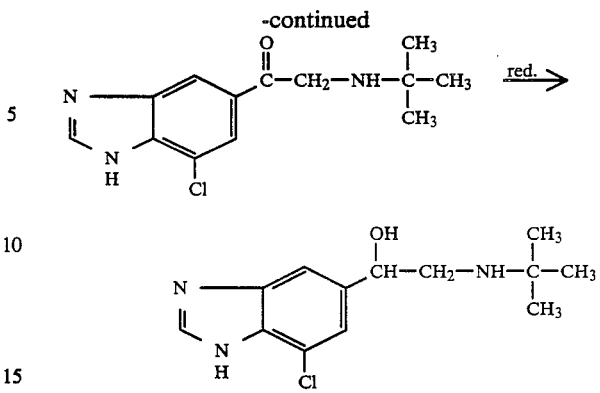

The compounds of the formula II are new in some cases. Their preparation is described below. The substituents $R^1$ and $R^2$ preferably have the preferred meanings given above. The following compounds of the formula II may be mentioned specifically: 5-benzimidazyl bromo-methyl keton, 5-benzimidazolyl chloromethyl ketone, 4-bromo-6-benzimidazolyl bromomethyl ketone and 4-bromo-6-benzimidazolylchloromethyl ketone.

The amines of the formula III are known (compare, for example, EP-OS (European Published Specification) 23,385). The substituents $R^4$ to $R^6$ preferably have the preferred meanings given above for the compounds of the formula I. The following amines of the formula III may be mentioned specifically: isopropylamine, isobutylamine, sec.-butylamine, tert.-butylamine, 2-amino-2-methyl-propan-1-l, 3-(4-carbomethoxyphenyl)-2-propylamine, 3 3-(4-methoxycarbonylmethoxyphenyl)-2-propylamine, -(4-carboxyphenyl)-2-propylamine, 3-(4-carboxymethoxy-phenyl)-2-propylamine, 3-(4-hydroxymethylphenyl)-2-propylamine, 3-(4-dimethylaminomethylphenyl)-2-propylamine and 3-(4-(2-hydroxyethyl)-phenyl)-2-propylamine.

The following reducing agents may be mentioned as reducing agents for carrying out process (3a): $H_2$/catalyst, and examples of the catalyst which may be mentioned are: $PtO_2$ and Pd-on-active charcoal; and complex metal hydrides, such as, for example, $LiAlH_4$, $NaBH_4$ and $NaBH_3CN$.

The following reducing agents are particularly preferably used: $NaBH_4$ and $NaBH_3CN$.

Process (3a) is carried out by bringing together the compounds II and III in a diluent in an approximately equimolar ratio and then carrying out the reduction.

The reduction is preferably carried out at temperatures from $-20°$ C. to $+100°$ C.

The reaction is preferably carried out under atmospheric pressure.

All the inert organic solvents can be used as diluteness. These include, in particular, aliphatic and aromatic hydrocarbons, such as pentane, hexane, cyclohexane, petroleum ether, ligroin, benzene and toluene; chlorinated hydrocarbons such as methylene chloride, ethylene chloride and chloroform; ethers, such as diethyl ether and glycol dimethyl ether; nitriles, such as acetonitrile, propionitrile and benzonitrile; and alcohols, such as methanol, ethanol and n- and i-propanol.

Alcohols are preferred, it being possible for the reduction to be carried out immediately without isolation of the intermediate stages.

If 1-(5-benzimidazolyl-1-hydroxy-2-chloroethane is used as the compound of the formula IV and 3-(4-carbomethoxyphenyl)-2-propylamine is used as the amine of the formula III in process 3b), process 3b) can be represented by the following equation:

formula VI in process 3c), process 3c) can be represented by the following equation:

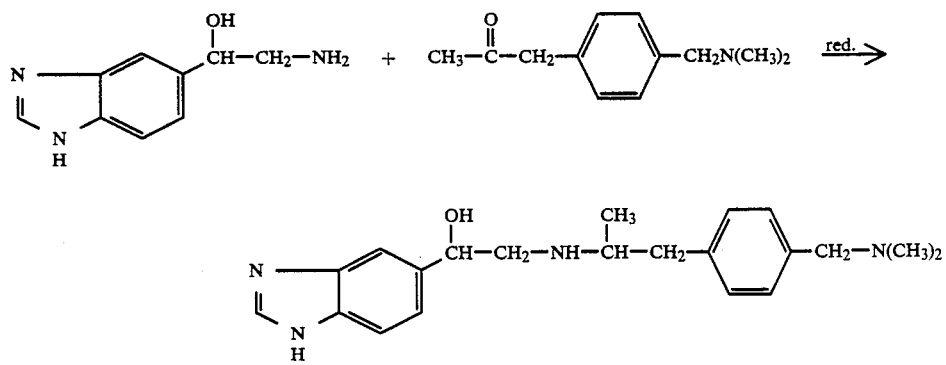

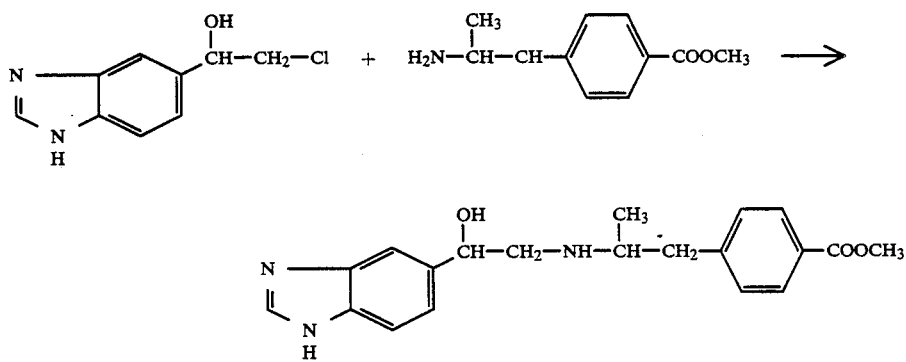

β-Halogenoethyl compounds of the formula IV are new. Their preparation is described below. The substituents $R^1$ to $R^3$ preferably have the preferred meanings given for the compounds of the formula I. The following compounds of the formula IV may be mentioned specifically: 1-(5-benziidazolyl)-2-chloroethanol, 1-(5-benzimidazolyl)-2-bromoethanol, 1-(4-bromo-6-benzimidazoyl)-2-chloroethnol, 1-(4-bromo-6-benzimidazolyl)-2-bromoethanol and 1-(4-chloro-6-benzimidazolyl-2-bromoethanol.

Process (3b) is carried out by reacting the β-halogenoethyl compound of the formula IV with excess amine of the formula III, if appropriate in the presence of a diluent.

The reaction is carried out at temperatures from +20° C. to +150° C.

The reaction is carried out under atmospheric pressure or under increased pressure.

All the inert organic solvents can be used as dilutents. These include, in particular, aliphatic and aromatic, optionally halogenated hydrocarbons, such as pentane, hexane, cyclohexane, benzene, toluene, methylene chloride and chloroform, and furthermore ethers, such as diethyl ether, tetrahydrofuran and dioxane, and moreover nitriles, such as acetonitrile and benzonitrile, and furthermore amides, such as dimethylformamide, and furthermore alcohols, such as methanol, ethanol and n- and i-propanol.

Alcohols are preferably used.

If 1-(5-benzimidazolyl-2-aminoethanol is used as the compound of the formula V and 4-(dimethylaminomethyl)phenylacetone is used as the compound of the The compounds of the formula V are known in some cases (compare, for example, DE-OS (German Published Specification) 2,754,148). New compounds of the formula V are described below. The substituents $R^1$ to $R^3$ preferably have the preferred meanings given above in the case of the compounds of the formula I. The following compounds of the formula V may be mentioned specifically. 1-(4-bromo-6-benzimidazolyl)-2-aminoethanol and 1-(4-chloro-6-benzimidazolyl)-2-aminoethanol.

Compounds of the formula VI are known (compare, for example, EP-OS (European Published Specification) 70,133). The substituents $R^5$ and $R^6$ preferably have the meanings given above in the case of the compounds of the formula I.

The following compounds of the formula VI may be mentioned specifically: acetone, methyl ethyl ketone, methyl isobutyl ketone, 4-carbomethoxyphenylacetone, 4-(carbomethoxymethoxy)phenylacetone and 4-(2-hydroxyethoxy)phenylacetone.

Process 3c) is carried out by taking up approximately equimolar amounts of the compounds of the formulae V and VI in a diluent and subjecting the mixture to reduction.

The reaction is carried out at temperatures from 0° C. to 150° C.

The reaction is preferably carried out under atmospheric pressure.

All the inert organic solvents can be used as diluents. These include aliphatic and aromatic, optionally halogenated hydrocarbons, such as pentane, hexane, cyclohexane, benzene, toluene, methylene chloride, ethylene chloride, chloroform and chlorobenzene, and furthermore ethers, such as diethyl ether, tetrahydrofuran and dioxane, and moreover nitriles, such as acetonitrile and benzonitrile, amides, such as dimethylformamide, and alcohols, such as methanol and ethanol.

Reducing agents which can be used are: H$_2$/catalyst, and PtO$_2$ may be mentioned as an example of a catalyst; and complex metal hydrides, such as, for example, LiAlH$_4$, NaBH$_4$ and NaBH$_3$CN.

If 5-benzimidazolyl is used as the compound of the formula VII and 3-(4-methoxyphenyl)-2-propylamine is used as the amine of the formula III in process (3d, process (3d) can be represented by the following equation:

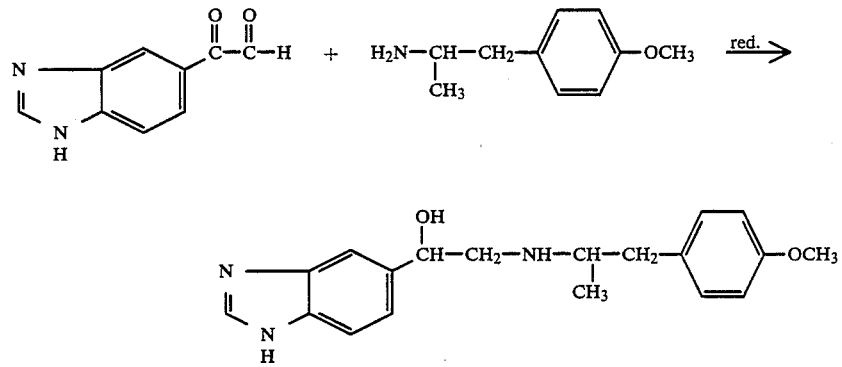

Compounds of the formula VII are new. Their preparation is described below. The substituents R$^1$ and R$^2$ preferably have the preferred meanings given above in the case of the compounds of the formula I. The following compounds of the formula VII may be mentioned specifically: 2-hydroxy-5-benzimidazolylglyoxal, 2-hydroxy-4-bromo-6-benzimidazolyglyoxal and 2-hydroxy-4-chloro-6-benzimidazolylglyoxal.

Process (3d) is carried out by adding approximately the equivalent amount of the amine of the formula III to the compound of the formula VII in a diluent and then carrying out the reduction.

The reaction is carried out at temperatures from 0° C. to 100° C.

The reaction is preferably carried out under atmospheric pressure.

All the inert organic solvents can be used as diluents. These include, in particular, aliphatic and aromatic, optionally halogenated hydrocarbons, such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, and furthermore ethers, such as diethyl and dibutyl ether, glycol dimethyl ether and diglycol dimethyl ether, tetrahydrofuran and dioxane, and in addition esters, such as methyl and ethyl acetate, and furthermore nitriles, such as, for example, acetonitrile, propionitrile, benzonitrile and glutaric acid dinitrile, and moreover amides, such as, for example, dimethylformamide, dimethylacetamide and N-methylpyrrolidone, as well as tetramethylene sulphone and hexamethylphosphoric acid triamide, and moreover alcohols, such as methanol, ethanol and n- and i-propanol.

Reducing agents which can be used are H$_2$/catalyst, and PtO$_2$ and Pd-on-charcoal may be mentioned as the catalyst; and furthermore complex metal hydrides, such as LiAlH$_4$ and NaBH$_4$.

As already mentioned, the new compounds of the formula II can be prepared by the processes described under 5.

If 5-acetylbenzimidazole is used as the compound of the formula VIII and bromine is used as the halogen Hal in process (5a), the reaction can be represented by the following equation:

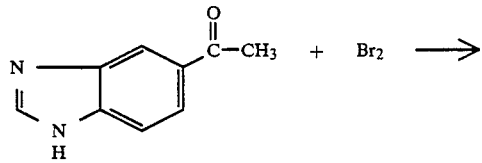

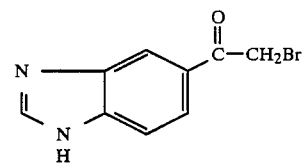

The compounds of the formula VIII are new. Their preparation is described below.

The following compounds of the formula VIII may be mentioned specifically: 5-acetylbenzimidazole, 4-chloro-6-acetylbenzimidazole and 4-bromo-6-acetylbenzimidazole.

Process (5a) is carried out by adding the equivalent amount of halogen, if necessary dissolved in a diluent, to the compound VIII in a diluent.

The reaction is carried out at +20° C. to +150° C., preferably at the boiling point of the diluent used.

The reaction is preferably carried out under atmospheric pressure.

Diluents which may be mentioned are: aliphatic, optionally halogenated hydrocarbons, such as pentane, hexane, heptane, cyclohexane, methylene chloride, ethylene chloride, chloroform, carbon tetrachloride, alcohols, such as methanol and ethanol, esters, such as ethyl acetate, and mixtures of these diluents.

If 4-chloro-6-acetylbenzimidazole is used as the compound of the formula VIII and copper(II) bromide is used as the compound of the formula CuHal$_2$ in process 5b), . the reaction can be represented by the following equation:

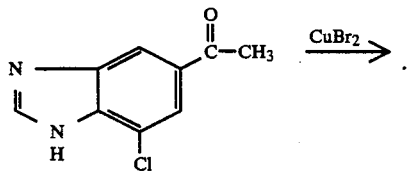

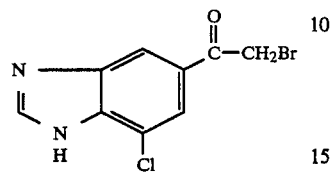

Process (5b) is carried out by heating equivalent amounts of the compound of the formula VIII and the compound CuHal₂ under reflux in the diluent for 1–24 hours, preferably 6–12 hours.

The other reaction parameters and the diluents are scribed in the case of process (5a).

As already mentioned, the new compounds of the formula VIII can be prepared by the process described under 7.

If 3,4-diaminoacetophenone is used as the compound of the formula IX in the process, the process can be represented by the following equation:

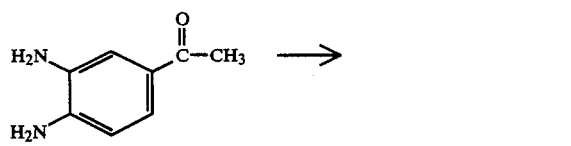

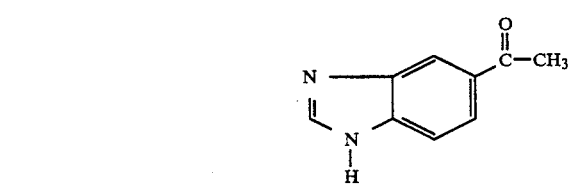

Compounds of the formula IX are known (JACS 80 (1958), 1657) or can be prepared by processes analogous to known processes. The radical $R^2$ preferably denotes hydrogen, $C_{1-4}$-alkyl, in particular methyl, chlorine or bromine. The following compounds of the formula IX may be mentioned specifically: 3-bromo-4,5-diaminoacetophenone and 3-chloro-4,5-diamino acetophenone.

The process is carried out by reacting a compound of the formula IX with formic acid in the presence of an inorganic acid.

The inorganic acids include hydrogen halide acids, such as hydrochloric acid, sulphuric acid and phosphoric acid. The reaction is carried out at temperatures from +20° C. to +120° C.

The reaction is preferably carried out in an aqueous solution of the inorganic acid. It is preferably carried out under atmospheric pressure.

As already mentioned, the new compounds of the formula VI can be prepared by the process described under g.

If 2-hydroxy-5-benzimidazolyl chloromethyl ketone is used as the compound of the formula II in process 9, the process can be represented by the following equation:

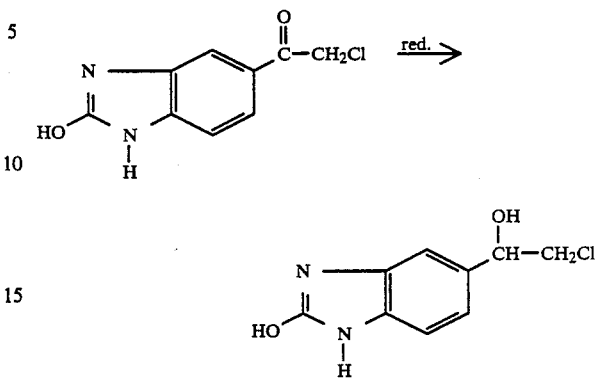

The substituents $R^1$, $R^2$ and Hal in the compounds of the formula II have the preferred meanings given above.

Reducing agents which may be mentioned for carrying out the process are: $H_2$/catalyst, and catalysts which may be mentioned are: $PtO_2$ and Pd-on-charcoal; and complex metal hydrides, such as, for example, $LiAlH_4$, $NaBH_4$ and $NaBH_3CN$. $NaBH_4$ and $NaBH_3CN$ are preferably used.

The process is carried out by reacting the compound II with the reducing agent in a diluent.

The reaction is carried out at temperatures from −20° C. to +100° C.

The reaction is preferably carried out under atmospheric pressure.

All the inert organic solvents can be used as diluents. These include, in particular, optionally halogenated aliphatic and aromatic hydrocarbons, such as pentane, hexane, cyclohexane, benzene, toluene, methylene chloride, chloroform and chlorobenzene; ethers, such as diethyl ether and tetrahydrofuran; nitriles, such as acetonitrile and benzonitrile, and alcohols, such as methanol, ethanol and n- and i-propanol. Alcohols are preferably used.

As already mentioned, the compounds of the formula V are known in some cases (for example from British Patent 1,559,915). The new compounds of the formula V are summarized under 10 (above). They are prepared by the process described under 11. The process is carried out analogously to the process described in British Patent 1,559,915.

As already mentioned, the new compounds of the formula VII can be prepared by the processes described under 13.

If(4-chloro-6-benzimidazolyl)chloromethyl ketone is used as the compound of the formula II in process (13a), the process can be represented by the following equation:

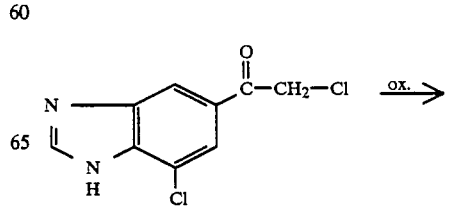

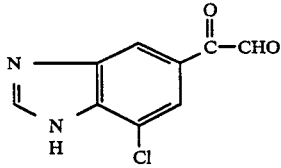

The compounds mentioned above are preferably used as the halogenomethyl ketones of the formula II.

Process (13a) is carried out by oxidizing the compounds of the formula II, if appropriate in the presence of a diluent.

The reaction is carried out at temperatures from +20° C. to +100° C.

The reaction is preferably carried out under atmospheric pressure.

Dimethyl sulphoxide is preferably used as the oxidizing agent (N. Kornblum et. al., JACS 79, 6562 (1957)).

If the reaction is carried out in the presence of a diluent, all the inert organic solvents can be used. These include, in particular, aliphatic and aromatic, optionally halogenated hydrocarbons, such as pentane, hexane, cyclohexane, benzene, toluene, methylene chloride, chloroform and chlorobenzene; ethers, such as diethyl ether and tetrahydrofuran; and nitriles, such as acetonitrile and benzonitrile. The reaction is preferably carried out in dimethyl sulphoxide without a further solvent.

If 4-bromo-6-acetylbenzimidazole is used as the compound of the formula VIII in process (13b), the process can be represented by the following equation:

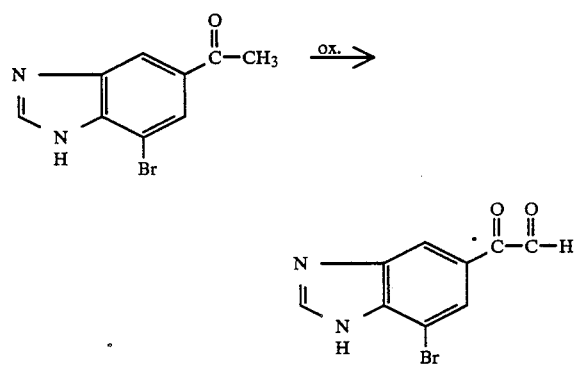

The process is carried out by oxidizing the compound of the formula VIII with selenium dioxide in the presence of a diluent (compare Org. React. 5(1949), 331).

The active compounds have a favorable toxicity towards warm-blooded animals and are suitable as agents for promoting the yield in breeding and stock animals. They are used here for promoting and accelerating growth and milk and wool production and for improving feed utilization and meat quality and for shifting the meat/fat ratio in favor of meat.

The stock and breeding animals include mammals, such as, for example, cattle, horses, sheep, pigs, goats, camels, water buffaloes, asses, rabbits, fallow deer, reindeer and fur-bearing animals, such as, for example, mink, chinchillas and raccoons, birds, such as, for example, chickens, geese, turkeys and ducks, and fresh- and saltwater fish, such as, for example, trout, carp and eels.

The active compounds are used during all the growth and yield phases of the animals, regardless of the sex of the animals. The active compounds are preferably used during the intensive growth and yield phase. The intensive growth and yield phase lasts from one month to 10 years, depending on the species of animal. The active compounds prove to be particularly useful for rearing and keeping young and fattening animals.

The active compounds are used enterally or parenterally directly or in the form of formulations suitable for animals. Enteral use of the active compounds is effected, for example, orally in the form of powders, tablets, capsules, pastes, drinks, granules or boli, via solutions, emulsions or suspensions for oral administration and via the feed or drinking water. Parenteral use is effected, for example, in the form of injection (intramuscular, subcutaneous, intravenous or by implants).

Formulations for administration by the feed or drinking water are to be emphasized in particular. The active compounds can thereby be added to the feed directly or in the form of premixes or feed concentrates.

Feed includes individual feedstuffs of vegetable origin, such as hay, beet, cereals and cereal by-products, molasses and silage, individual feedstuffs of animal origin, such as meat, fats, milk products, bone meal and fish products, individual feedstuffs such as vitamins, proteins, sugars, starch and meals, amino acids, for example DL-methionine, and salts, such as lime and sodium chloride. Feed also includes supplements, ready-made and mixed feedstuffs. These contain individual feedstuffs in a composition which ensures balanced nutrition in respect of energy and protein supply and the supply of vitamins, mineral salts and trace elements.

Premixes and feed concentrates are mixtures of the active compound with carriers and if appropriate other auxiliaries. The carriers include all the individual feedstuffs or mixtures thereof.

The active compounds can be present in the formulations by themselves or as mixtures with other yield-promoting active compounds, mineral feedstuffs, trace element compounds, vitamins, nitrogen-containing non-protein compounds, dyestuffs, antioxidants, aroma substances, emulsifiers, flow control auxiliaries, preservatives and pressing auxiliaries.

Other yield-promoting active compounds are, for example, antibiotics, such as tylosin and virginamycin. Mineral feedstuffs are, for example, dicalcium phosphate, magnesium oxide and sodium chloride.

Trace element compounds are, for example, iron fumarate, sodium iodide, cobalt chloride, copper sulphate, zinc oxide and selenium compounds.

Vitamins are, for example, vitamin A, vitamin $D_3$ and vitamin E.

Nitrogen-containing non-protein compounds are, for example, biuret and urea.

Dyestuffs are, for example, carotinoids, such as canthaxidine, zeaxanthine, capsanthine or dyestuffs which are approved for coloring foodstuffs.

Antioxidants are, for example, ethoxyquin, butylhydroxytoluene and ascorbic acid.

Aroma substances are, for example, vanillin.

Emulsifiers are, for example, esters of lactic acid and lecithin.

Flow control auxiliaries are, for example, sodium stearate, calcium stearate, silicic acids, bentonites and lignin-sulphonates.

Preservatives are, for example, propionic acid, calcium propionate, sorbic acid and ascorbic acid.

Pressing auxiliaries are, for example, ligninsulphonates and cellulose ethers.

The concentration of the active compounds in the feed is usually about 0.001–500 ppm, preferably 0.1–50 ppm.

The concentration of the active compounds in the premixes or feed concentrates is about 0.5 to 50 per cent by weight, preferably 1 to 20 per cent by weight.

The amount of active compounds administered to the animals for achieving the desired effect can be varied substantially because of the favorable properties of the active compounds. It is preferably about 0.001 to 50 mg/kg, in particular 0.01 to 5 mg/kg of body weight per day. The appropriate amount of active compound and the appropriate duration of the administration depend in particular on the species, the age, sex, state of health and type of housing and feeding of the animals and can easily be determined by any expert.

The active compounds are administered to the animals by the customary methods. The nature of the administration depends in particular on the species, behavior and state of health of the animals.

The active compounds can be administered a single time. However, the active compounds can also be administered temporarily or continuously throughout the entire or throughout part of the growth and yield phase. In the case of continuous administration, they can be used once or several times daily at regular or irregular intervals.

Example of the composition of a chick-rearing feed containing the active compound according to the invention:

200 g of wheat, 340 g of corn 361 g of shredded soya, 60 g of beef tallow, 15 g of dicalcium phosphate, 10 of calcium carbonate, 4 g of iodonated sodium chloride, 7.5 g of a vitamin/mineral mixture of the composition shown below and 2.5 g of active compound premix of the composition shown below gives, after thorough mixing, 1 kg of feed.

1 kg of vitamin/mineral mixture contains: 600 I.U. of vitamin A, 100 I.U. of vitamin $D_3$, 10 mg of vitamin E, 1 mg of vitamin $K_3$, 3 mg of riboflavin, 2 mg of pyridoxine, 20 mcg of vitamin $B_{12}$, 5 mg of calcium pantothenate, 30 mg of nicotinic acid, 200 mg of choline chloride, 200 mg of $MnSO_4 \times H_2O$, 140 mg of $ZnSO_4 \times 7H_2O$, 100 mg of $FeSO_4 \times 7H_2O$ and 20 mg of $CuSO_4 \times 5\ H_2O$ in cereal flour as the carrier.

1 kg of active compound premix contains 100 g of active compound and 900 g of wheat flour. Example of the composition of a pig-rearing feed containing the active compound according to the invention:

630 g of shredded cereal feed (composed of 200 g of corn, 150 g of shredded barley, 150 g of shredded oats and 130 g of shredded wheat), 80 g of fish meal, 60 g of shredded soy beans, 60 g of tapioca meal, 38 g of brewer's yeast, 50 g of a vitamin/mineral mixture (composition as for the chick feed) 30 g of linseed cake, 30 g of corn gluten feed,, 10 g of soy bean oil, 10 g of cane sugar molasses and 2 g of active compound premix give, after thorough mixing, 1 kg of feed. 1 kg of active compound premix contains 200 g of active compound, 20 g of vegetable oil and 780 g of calcium carbonate powder. Example of the composition of a cattle feed containing the active compound according to the invention:

69.95 % of shredded cereal feed, 10 % of ground corn cobs, 8 % of soy bean meal, 5 % of lucerne meal, 5 % of molasses, 0.6 % of urea, 0.5 % of calcium phosphate, 0.5 % of calcium carbonate, 0.3 % of sodium chloride, 0.15% of a vitamin/mineral mixture and 0.2% of active compound premix of the composition shown for the pig-rearing feed. The vitamin/mineral mixture contains, per kg, 70,000 I.U. of vitamin A, 70,000 of vitamin $D_3$, 100 mg of vitamin E, 50 mg of $MnSO_4 \times H_2O$ and 30 mg of $ZnSO_4 \times 7\ H_2O$ in cereal flour as the carrier.

The active compound premix is admixed to the vitamin/mineral mixture in the required amount and this mixture is then mixed thoroughly with the other constituents.

EXAMPLE

Rat feeding experiment

Female laboratory rats weighing 90–110 g of the SPF Wistar type (breeder Hagemann) are fed ad lib with standard rat feed to which the desired amount of active compound has been added. Each experiment set-up is carried out with feed of an identical batch, so that differences in the composition of the feed cannot impair the comparability of the results.

The rats are given water ad lib.

In each case 12 rats form a test group and are fed on feed to which the desired amount of active compound has been added. A control group is given feed without active compound. The test groups are composed so that the average body weight and the scatter in the body weights of the rats is the same in each test group, so that comparability of the test groups with one another is ensured.

The animals are acclimatized to the new housing conditions for 2 days before the start of the experiment, and during this period feed without added active compound is supplied. The animals are then given feed containing the active compound for 13 days. The relative weight increase in relation to the untreated control is determined.

The results which can be seen from the table are obtained:

TABLE

Rat feeding experiment

| Active compound Example No. | Active compound concentration [ppm] | Relative weight increase [%] |
|---|---|---|
| 1 | 50 | 25 |
| 2 | 50 | 11 |
| 3 | 50 | 22 |

EXAMPLES 1. 1-(5-Benzimidazolyl-2-tert.-butylaminoethanol

Preparation by process(3a):

1.5 g (4.7 mmol) of 5-benzimidazolylbromomethyl ketone hydrobromide are added all at once to a solution of 2.5 g (34 mmol) of tert.-butylamine in 50 ml of methanol at room temperature and the mixture is heated to about 40° C. and stirred for 30 minutes. It is then cooled to 0° C., 300 mg (7.9 mmol) of $NaBH_4$ are added and the mixture is stirred for 30 minutes. It is then evaporated, the residue is partitioned between ethyl acetate and water and the organic phase is separated off, dried over $Na_2SO_4$ and evaporated.

Yield: 950 mg (87%); melting point 70° C.

Preparation by process (3d):

500 mg (2.3 mmol) of 5-benzimidazolylglyoxal and 730 mg (10 mmol) of tert.-butylamine are stirred in 50 ml of absolute methanol at room temperature for 12 hours, after addition of a little molecular sieve. The mixture is then cooled to 0° C. and 180 mg (5 mmol) of $NaBH_4$ are added. After 30 minutes, the mixture is evaporated and the residue is partitioned between ethyl acetate and water. The organic phase is separated off, dried over Na₂SO₄ and evaporated.

Yield: 375 mg (70%), melting point 70° C.

2. 1-(4-Bromo-6-benzimidazolyl)-2-tert.-butylaminoethanol prepared in accordance with process (3d)

Yield: 71 %; melting point 68° C.

3. 1-(5-Benzimidazolyl)-2-(2-[3-[4-(2-hydroxyethoxyphenyl]-propyl]amino)ethanol prepared in accordance with process (3d)

Yield: 70%, melting point 112° C.

4. 1-(2-Hydroxy-5-benzimidazoyl)-2-tert.-butylaminoethanol prepared in accordance with process (3a)

Yield: 75%, melting point 85° C. 5. 5-Acetylbenzimidazole

A mixture of 2 g (13.3 mmol) of 3,4-diaminoacetophenone, 0.92 g (20 mmol) of formic acid and 15 ml of 4N hydrochloric acid is heated under reflux. After 15 minutes, the mixture is cooled, diluted with 50 ml of water and washed three times with 25 ml of ethyl acetate each time. The aqueous phase is rendered alkaline with concentrated ammonia and extracted three times with 25 ml of ethyl acetate each time. The combined organic phases are dried over Na₂SO₄ and evaporated. 2 g (94% of theory) of a red-brown oil remain. $^1$H-NMR (DMSO-$d_6$, δ(ppm)): 2.65 (s,3H); 7.65 (m,1); 7.85 (d,1H); 8.3 (m,1H); 8.45 (s,1H); 12.8 (s,1H).

6. 5-(Bromoacetyl)benzimidazole hydrobromide 1.21 g (7.6 mmol) of bromine in 5 ml of glacial acetic acid are added to a solution of 1.2 g (7.5 mmol) of 5-acetylbenzimidazole and 1.35 g of 48% strength aqueous HBr (=8 mmol of HB) in 15 ml of glacial acetic acid at room temperature. The mixture is stirred at 40° C. for 30 minutes and cooled and the product which has precipitated out is filtered off.

Yield: 1.5 g (63% of theory), melting point >250° C. $^1$H-NMR (CD₃OD, δ(ppm)): 4.8 (s,2H); 7.9 (dd,1H); 8.2 (dd,1h); 8.5 (d,1H); 9.4 (s,1H).

It will be appreciated that the instant specification and claims are set forth by way of illustration and not limitation, and that various modifications and changes may be made without departing from the spirit and scope of the present invention.

What is claimed is:

1. A method of promoting the yield and growth of healthy animals which comprises administering to such animals a yield and growth promoting effective amount of a benzimidazole derivative of the formula

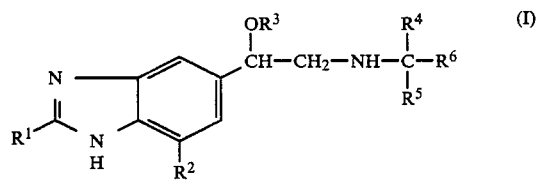

in which
  $R^1$ stands for hydrogen, hydroxyl, alkyl or halogenoalkyl,
  $R^2$ stands for hydrogen, alkyl, halogen, CN or halogenoalkyl,
  $R^3$ stands for hydrogen, alkyl or acyl,
  $R^4$ stands for hydrogen, alkyl or halogenoalkyl,
  $R^5$ stands for alkyl or halogenoalkyl,
  $R^6$ stands for alkyl or cycloalkyl, which is optionally substituted by halogen, cycloalkyl, OH, alkoxy, halogenoalkoxy or aryl, which can in turn be substituted by alkyl, halogen, CN or the radicals —COR⁷, —O—alkylene-COR⁷, -alkylene-R⁸ or —O—alkylene-R⁸,
  $R^7$ stands for hydroxyl, alkoxy or —NR⁹R¹⁰,
  $R^8$ stands for hydroxyl, alkoxy or —NR⁹R¹⁰,
  $R^9$ stands for hydrogen or alkyl and
  $R^{10}$ stands for hydrogen or alkyl, or a physiologically tolerated salt thereof.

2. The method according to claim 1, in which
  $R^1$ stands for H or OH,
  $R^2$ stands for H, halogen, CN or halogenalkyl,
  $R^3$ stands for H,
  $R^4$ stands for H or $C_{1-4}$-alkyl,
  $R^5$ stands for $C_{1-4}$ alkyl,
  $R^6$ stands for $C_{1-4}$-alkyl, which is optionally substituted by halogen, OH, $C_{1-4}$-alkoxy, $C_{1-4}$-halogenoalkoxy or phenyl, which is optionally substituted by $C_{1-4}$-alkyl, COR⁷, —O—$C_{1-3}$-alkylene-COR⁷, $C_{1-3}$-alkylene-R⁸ or O-$C_{1-3}$-alkylene-R⁸,
  $R^7$ stands for OH, $C_{1-4}$-alkoxy, amino, methylamino or dimethylamino and
  $R^8$ stands for OH, $C_{1-4}$-alkoxy, amino, methylamino or dimethylamino.

3. The method according to claim 1, in which
  $R^1$ stands for hydrogen or OH,
  $R^2$ stands for hydrogen, clorine, bromine or trifluoromethyl,
  $R^3$ stands for hydrogen,
  $R^4$ stands for hydrogen or methyl,
  $R^5$ stands for methyl and
  $R^6$ stands for methyl, which is optionally substituted by OH or phenyl, which is in turn optionally substituted by methyl, ethyl, methoxyethyl, hydroxyethyl, methoxyethoxy or hydroxyethoxy.

4. The method according to claim 1, wherein such compound is 1-(5-benzimidazolyl)-2-tert.-butylaminoethanol of the formula

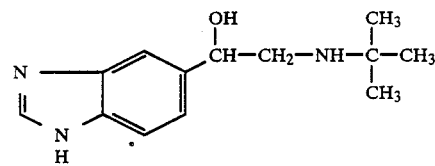

or a physiologically tolerated salt thereof.

5. The method according to claim 1, wherein such compound is 1-(4-bromo-6-benzimidazolyl)-2-tert.-butylaminoethanol of the formula

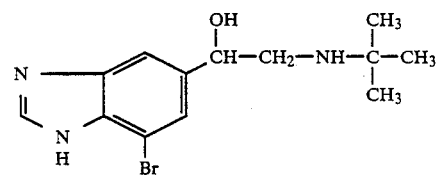

or a physiologically tolerated salt thereof.

6. The method according to claim 1, wherein such compound is 1-(5-benzimidazolyl)-2-(2-[3-[4-(2-hydroxyethoxyphenyl]-propyl]amino)ethanol of the formula

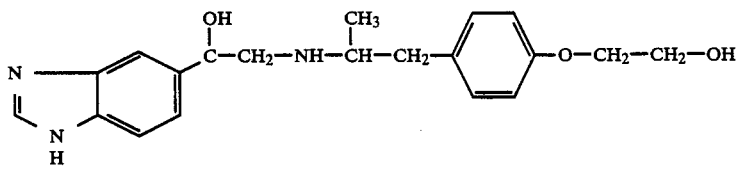

or a physiologically tolerated salt thereof.

7. The method according to claim 1, wherein such compound is 1-(2-hydroxy-5-benzimidazolyl)-2-tert.-butylaminoethanol of the formula

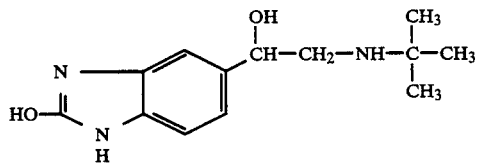

or a physiologically tolerated salt thereof.

8. An animal feed comprising a foodstuff and a yield and growth promoting effective amount of a benzimidazole derivative of the formula

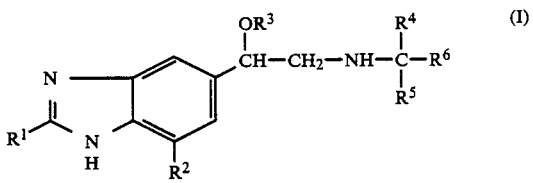

in which
$R^1$ stands for hydrogen, hydroxyl, alkyl or halogenoalkyl,
$R^2$ stands for hydrogen, alkyl, halogen, CN or halogenoalkyl,
$R^3$ stands for hydrogen, alkyl or acyl,
$R^4$ stands for hydrogen, alkyl or halogenoalkyl,
$R^5$ stands for alkyl or halogenoalkyl,
$R^6$ stands for alkyl or cycloalkyl, which is optionally substituted by halogen, cycloalkyl, OH, alkoxy, halogenoalkoxy or aryl, which can in turn be substituted by alkyl, halogen, CN or the radicals —$COR^7$, —O—alkylene-$COR^7$, —alkylene—$R^8$ or —O—alkylene-$R^8$,
$R^7$ stands for hydroxyl, alkoxy or —$NR^9R^{10}$,
$R^8$ stands for hydroxyl, alkoxy or —$NR^9R^{10}$,
$R^9$ stands for hydrogen or alkyl and
$R^{10}$ stands for hydrogen or alkyl,
or a physiologically tolerated salt thereof.

* * * * *